United States Patent [19]
Yamaguchi

[11] Patent Number: 4,557,254
[45] Date of Patent: Dec. 10, 1985

[54] ENDOSCOPE

[75] Inventor: Tathuya Yamaguchi, Hino, Japan

[73] Assignee: Olympus Optical Co., Ltd., Japan

[21] Appl. No.: 616,112

[22] Filed: Jun. 1, 1984

[30] Foreign Application Priority Data

Jun. 13, 1983 [JP] Japan .............................. 58-90229[U]

[51] Int. Cl.⁴ ............................................... A61B 1/06
[52] U.S. Cl. ......................................................... 128/4
[58] Field of Search ........................................ 128/4, 6

[56] References Cited

U.S. PATENT DOCUMENTS

| 3,788,303 | 1/1974 | Hall | 128/4 |
| 3,799,151 | 3/1974 | Fukaumi et al. | 128/6 |
| 3,892,228 | 7/1975 | Mitsui | 128/4 |
| 4,203,430 | 5/1980 | Takahashi | 128/4 |
| 4,273,111 | 6/1981 | Tsukaya | 128/6 |
| 4,294,233 | 10/1981 | Takahashi | 128/4 |
| 4,483,326 | 11/1984 | Yamaka et al. | 128/4 |

FOREIGN PATENT DOCUMENTS

| 2747653 | 5/1978 | Fed. Rep. of Germany | 128/4 |
| 136523 | 10/1981 | Japan . | |
| 880639 | 10/1961 | United Kingdom | 128/4 |

Primary Examiner—William H. Grieb
Attorney, Agent, or Firm—Ostrolenk, Faber, Gerb & Soffen

[57] ABSTRACT

An endoscope including an inserting passage for accommodating a roller chain which operates a bendable portion located at the end of the endoscope. The endoscope also includes a loose-roller-chain accommodating chamber in which the loosened roller chain section is gathered. The accommodation chamber has a length from one corner to another corner measured in the longitudinal direction of the roller chain which is slightly larger than an integer times the length of the pitch between adjoining rollers of the roller chain. The pitch is the distance between rollers when link plates of the roller chain are alternatively bent in opposite directions. This occurs when the roller chain is compressed and shrunk lengthwise in order to prevent the roller chain from being jammed between opposite corners of the accommodation chamber.

8 Claims, 4 Drawing Figures

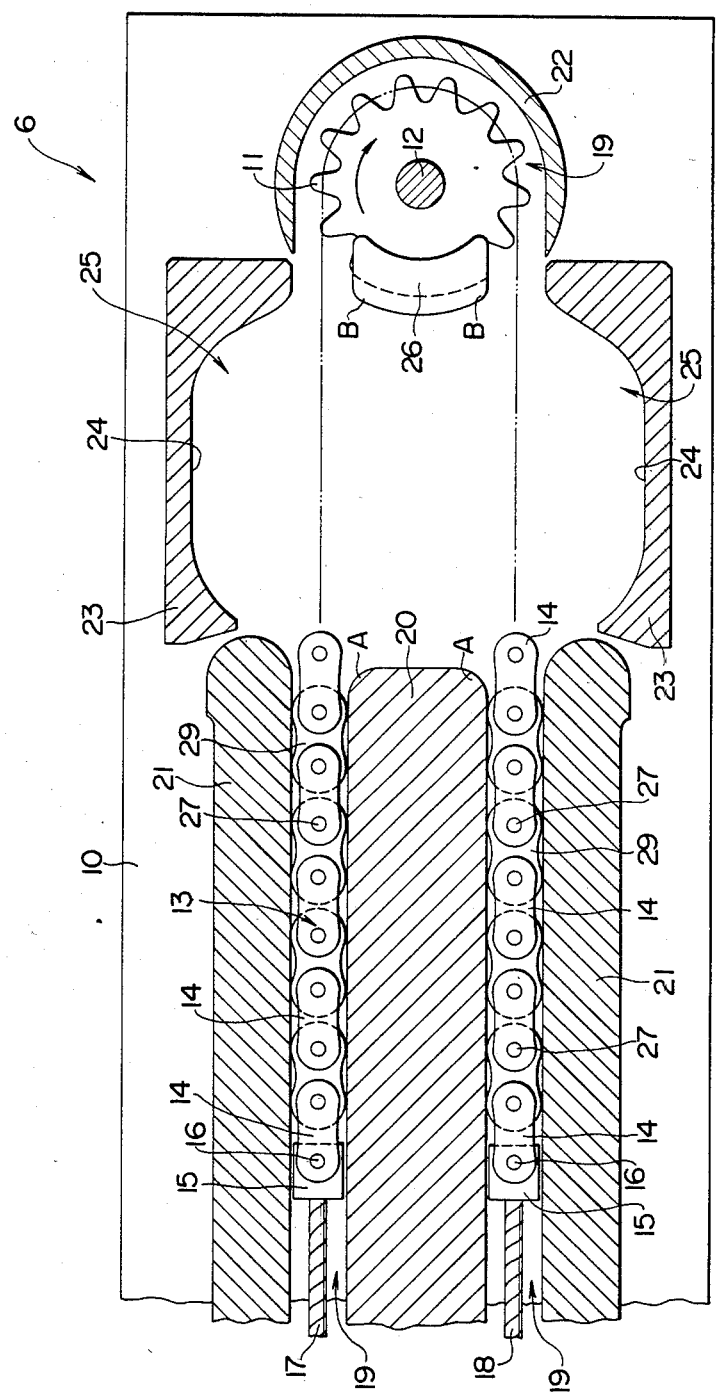

ENDOSCOPE

BACKGROUND OF THE INVENTION

The present invention relates to an endoscope, and more particularly, to an improvement in the bending mechanism located at the operating portion of the endoscope and which is used for bending a bendable portion of the endoscope.

In general, an endoscope comprises a bendable portion which is located at the front end of an inserting portion and an operating portion which is located at the rear end of the insertable portion in such a manner that the bendable portion can be remotely operated to bend as required by operating the operating portion. Specifically, a sprocket is provided in the operating portion which cooperates with an operating knob to engage a roller chain. Each opposite end of the roller chain is connected to one end of a pair of operating wires which in turn are connected through the inside of the insertable portion to the bendable portion. Accordingly, when the sprocket is rotated with the operating knob, one of the operating wires is pulled by the roller chain and the other operating wire loosens, to permit the bendable portion to be bent in one direction.

With the above construction when one of the operating wires loosens due to the rotation of the operation knob, it tends to move in a zigzag course or get into a peculiar bent shape if the looseness is not removed. When the bendable portion is operated repeatedly in such condition, there is a possibility of the operating wire being cut. Therefore, it is necessary to remove looseness of the operating wire.

In prior art devices, to remove looseness of the operating wire, an inserting passage is formed within the operating portion along the roller chain and a looseness accommodation portion is provided in a part of the inserting passage which is wider in the transverse direction than the remainder of the inserting passage so that the roller chain can be bent within the accommodation portion when the operating wire loosens. Using such a technique, however, where the roller chain is bent within the accommodation portion, it still may happen that link plates of the roller chain located at opposite end positions of the accommodation portion, in the longitudinal direction, are brought into a state where the link plates fall into corners of the accommodation portion. Namely, this happens when the length of the bent portion of the roller chain becomes substantially equal to the length of the accommodation portion in the longitudinal direction. In such a case, even when the operating wire is pushed and pulled, the part of the roller chain fallen in the accommodation portion stops moving. As a result, the bendable portion cannot be restored to its straight condition and the inserting portion may not be pulled out from a coeliac cavity without causing a serious accident.

SUMMARY OF THE INVENTION

It is an object of the invention to provide an endoscope which prevents jamming of a roller chain a portion of which is bent within a looseness accommodation portion when an operating wire is loosened. Thereby, a bendable portion can be always reliably operated.

According to the invention, the endoscope is provided with a looseness accommodation portion which allows the loose portion of a roller chain to be confined in part of an inserting passage through which the roller chain is movable. The length from one corner to an opposite corner of the accommodation portion in the direction along which the roller chain moves is deliberately set to be slightly larger than an integer times the length of a pitch between two adjoining rollers, measured on one side, under the condition when link plates of the roller chain are bent alternately in opposite directions to shrink the roller chain. Thereby, the likelihood of causing the roller chain to jam with opposite ends of the bent part of the roller chain stuck in the accommodation portion between opposite corners of the accommodation portion in the longitudinal direction is prevented. As a result, it is possible to reliably operate the bendable portion in a bendable manner with the operating knob which is located in the front side of the inserting portion.

BRIEF DESCRIPTION OF THE DRAWINGS

FIG. 2 is an enlarged plan view of the essential parts of a bending operation device which is disposed within an operating portion of the endoscope shown in FIG. 1;

DESCRIPTION OF A PREFERRED EMBODIMENT

Figure 1:
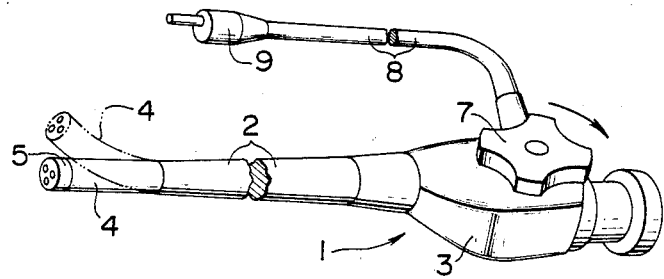
FIG. 1 is an exterior perspective view of an embodiment of an endoscope according to the invention.

Referring now to FIG. 1, an endoscope 1 comprises, in consecutive order, an operating portion 3 which is located on the rear end of an insertable portion 2, a bendable portion 4 and a distal rigid portion 5 which are located on the front end of the insertable portion 2. The operating portion 3 is provided with an operating knob 7 which operates a bending device 6 to be described later such that the bendable portion 4 can be operated to bend by rotating the knob 7. A light guide cable 8 is routed out from the operating portion 3, and its terminal end a connector 9 is provided which is connected to a light source (not shown).

The bending device 6 is constructed as shown in FIG. 2. Specifically, a base plate 10 is provided within the operating portion 3 and a shaft 12 on which a sprocket 11 is fixed is rotatably mounted on the upper side surface of the base plate 10. The operating knob 7 which is located outside the operating portion 3 is fixed to the shaft 12 at its one end.

The sprocket 11 engages a roller chain 13. The opposite ends of the roller chain extend longitudinally from the operating portion 3 to the insertable portion 2. Coupling members 15 are pivotally held by pins 16 on a pair of pin link plates 14 at the opposite ends of the roller chain 13, respectively. A first operating wire 17 and a second operating wire 18 are connected to the coupling members 15 at respective opposite ends of these wires. The other ends of these wires lead to the bendable portion 4 (see FIG. 1) where these other ends are coupled to the endmost of a plurality of joint rings (not shown) forming the bendable portion 4 which are rotatably coupled to each other.

An inserting passage 19 is formed on the upper surface of the base plate 10 along the roller chain 13. Specifically, on the upper surface of the base plate 10 are provided a central partition 20 which is located between the two opposite sections of roller chain 13, and a pair of first side partitions 21 which are located spacedly on either opposite side of the central partition 20. A circular arc shaped end partition 22 which is disposed in such a manner that it is spaced from but encircles a substantial semicircle of the sprocket and a pair of second side partitions 23 which are disposed between the opposite ends of the end partition 22 and the respective ends of the first side partitions 21 in the longitudinal direction, so as to form the inserting passage 19 with these partitions is also formed on the base plate 10. Recesses 24, 24 are provided in the second side partitions 23, 23 on their inner sides to extend from the inserting passage 19 to form a looseness accommodation portion 25 whose width between recesses 24, 24 in the transverse direction is sufficiently larger than the inserting passage 19 so that the roller chain 13 is bendable within the accommodation portion 25. Furthermore, a protector 26 is provided in close proximity to a part of the sprocket 11 on the opposite side of the end partition 22 such that when one side of the roller chain 13 loosens the loosened chain portion is prevented from being caught by the sprocket 11. The inserting passage 19 is covered by a cover plate (not shown).

Figure 3:
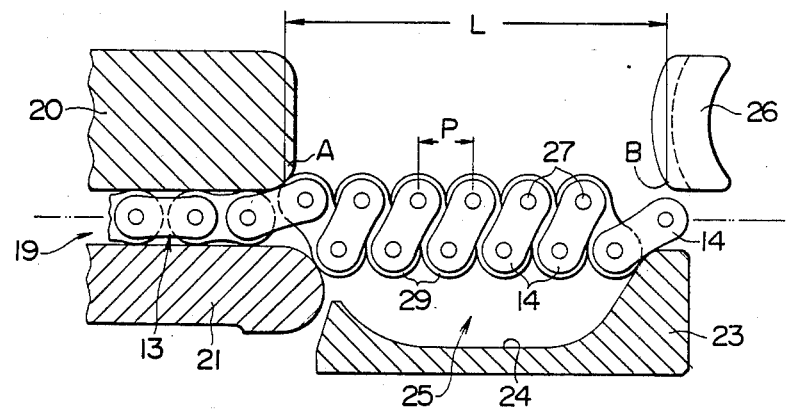
FIG. 3 is a plan view of the essential parts of the bending operation device shown in FIG. 2 in which a roller chain is in bent condition.

The length of the accommodation portion 25 in the longitudinal direction of the roller chain 13 is defined as follows. As shown in FIG. 3, assuming that A represents a corner of the central partition 20 opposite the accommodation portion 25 and B represents a corner of the protector 26, a length L between A and B is slightly larger than an integer times the length of a pitch P between rollers of the roller chain 13, which adjoin each other, when the pin link plates 14 and roller link plates 29 are fully pivoted when the chain is compressed and are alternately bent in opposite directions as shown in FIG. 3. That is, $$L = nP + \alpha \tag{1}$$

where n is an integer and $\alpha$ is a length smaller than P, preferably $\alpha \approx \frac{1}{2}P$. In other words, the length L is defined in such a manner that when link plates 14, 29 of the roller chain 13 are bent alternately, link plates which are positioned at the opposite ends of the bent part of the roller chain 13, namely, in the embodiment the roller link plates 29 as shown in FIG. 3, are prevented from falling between the corner A of the central partition 20 and the corner B of the protector 26.

With the endoscope 1 of the invention which includes the bending device 6 of the structure as described above, when the sprocket 11 is rotated by means of the knob 7 in the direction indicated with an arrow in FIG. 2, the roller chain 13 moves due to the rotation of the sprocket 11 and the first operating wire 17 is pulled while the second operating wire 18 loosened. Thus, the bendable portion 4 is bent as shown by the dashed-line of FIG. 1.

During bending, when the second operating wire 18 is loosened, pin link plates 14 and roller link plates 29 of the roller chain 13 on the side to which the second operating wire 18 is connected are bent within the accommodation portion 25 as shown in FIG. 3. When the length of the bent portion of the roller chain 13 is substantially equal to the length L between the corner A of the central partition 20 and the corner B of the protector 26 in the longitudinal direction of the accommodation portion 25, opposite ends of the bent portion of the roller chain 13 will be caught between the corners A and B, causing the roller chain 13 to stop running even when the sprocket 11 is rotated. In the endoscope 1 of the invention, however, the length L between the corners A and B is slightly larger than an integer times the length of the pitch P of the rollers. Hence, the length of the bent portion of the roller chain 13 which is located within the accommodation portion 25 is smaller than the length between the corners A and B of the accommodation portion 25. As a result, since there is no likelihood that link plates at the opposite ends of the bent portion of the roller chain 13 in the accommodation portion 25 remain in their former orientation in the accommodation portion and thus the roller chain 13 is prevented from being jammed while the sprocket 11 is still rotated. In other words, there is no possibility of causing such an accident that the bendable portion 4 is not returnable to its original state from a bent position.

Figure 4:
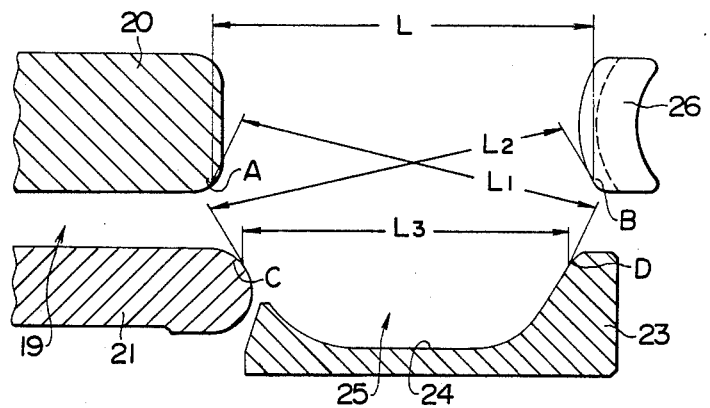
FIG. 4 is a diagram of dimensions between corners of a looseness accommodation portion in the bending operation device shown in FIG. 2.

In the above mentioned embodiment, it is referred to only the case that the length between both corners A and B is assumed as the length from one corner to the other one of the accommodation portion 25. However, as shown in FIG. 4, assuming that C represents a corner of the first side partition 21 and D represents a corner of the second side partition 23, and that $L_1$ represents the length between A and D, $L_2$ represents the length between C and B and $L_3$ represents the length between C and D, these lengths $L_1$, $L_2$ and $L_3$ may be also defined as $(nP + \alpha)$ in a manner similar to the length L between A and B so that the occurrence of the state that opposite ends of the bent portion of the roller chain 13 within the accommodation portion 25 fall in between one corner A or C and the other corner B or D in the longitudinal direction of the accommodation portion 25 can be avoided. In other words, when the four lengths L, $L_1$, $L_2$ and $L_3$ from one corner to the other corner of the accommodation portion 25 are defined as $(nP + \alpha)$, there is no possibility that the roller chain 13 stops running under any circumstances of bending of the roller chain 13 within the accommodation portion 25.

What is claimed is:

1. An endoscope comprising:

a sprocket disposed within an operating portion of the endoscope and manually operable means for rotating said sprocket, a roller chain which engages said sprocket, said roller chain including link plates which are pivotally connected to one another by respective rollers;

a pair of operating wires, one end of each of said wires being connected to a respective opposite end of said roller chain, the other end of each of said wires being coupled through the inside of an inserting portion of the endoscope to a bendable portion of the endoscope which is located at one end of said inserting portion;

an inserting passage formed within said operating portion for guiding said roller chain therein; and a looseness accommodation portion formed in part of said inserting passage with its transverse width being larger than that of the adjacent part of the inserting passage to permit said roller chain to form a bent configuration within said accommodation portion wherein said link plates of the roller chain are alternately bent in opposite directions with the result that the effective longitudinal length of said roller chain is reduced, the size and shape of said accommodation portion being so related to the size and shape of said chain that said chain cannot become stuck in said accommodation portion even when the maximum number of links of said chain are located in said accommodation portion under the condition that they are alternatively bent in opposite directions.

2. An endoscope according to claim 1 in which said inserting passage comprises a central partition disposed between opposite end portions of said roller chain, a pair of first partitions spacedly disposed on opposite sides of said central partition, a circular arc shaped end partition disposed to spacedly encircle a substantial portion of the circumference of said sprocket and a pair of second side partitions disposed between the opposite ends of said end partition and each one end of said first side partitions.

3. An endoscope according to claim 2 in which said looseness accommodation portion comprises the inner space defined by the inner sides of said pair of second side partitions.

4. An endoscope according to claim 2 further including a protector disposed adjacent to said sprocket for preventing a loosened portion of said roller chain from being caught on the sprocket.

5. An endoscope according to claim 4 wherein said first and second corners of said accommodation portion comprise a corner of said central partition and a corner of said protector, respectively.

6. An endoscope of claim 5 wherein each of the lengths between the corner of said central partition and a corner of said second side partition adjacent said protector, between a corner of said first side partition and the corner of said protector, and between the corner of said first side partition and the corner of said second partition adjacent said protector are also larger than a respective integer times said pitch p by a portion of said pitch p.

7. An endoscope according to claim 1, wherein said accommodation portion has a length as measured along the direction of running of said chain through said accommodation portion and between first and second opposite corners of said accommodation portion, which corners are adjacent said chain when it is in said bent configuration within said accommodation portion, which length is larger, by a fraction of a pitch p, than $n \times p$ wherein n is a positive integer greater than 1 and p is the pitch between adjacent rollers of said roller chain when said roller chain is in said bent configuration.

8. An endoscope comprising: an operating portion including a sprocket disposed within said operating portion and an operating knob for rotating said sprocket externally of said operating portion; a bendable portion; an insertable portion extending between said operating portion and said bendable portion, said insertable portion having an inserting internal passage along at least a portion thereof; a roller chain having rollers and link plates for pivotally interconnecting said rollers to form said roller chain, said roller chain engaging said sprocket; a pair of operating wires, each respective one end thereof being connected to a respective end of said roller chain; and a loose-roller-chain accommodation portion extending from said inserting passage into said operating portion, said accommodation portion having a transverse width which is larger than the width of said inserting passage, the width of said accommodation portion being sufficient to allow said rollers and said link plates of said roller chain to be squeezed together to form a squeezed portion which longitudinally shortens said roller chain along a portion thereof in said accommodation portion through pivoting of said link plates, said squeezed portion having a pitch p between adjacent rollers thereof, said accommodation portion having a length measured from a first respective corner thereof to another respective opposite corner thereof which is larger, by a fraction of said pitch, than $n \times p$, wherein n is an integer.

* * * * *